United States Patent [19]

Carr

[11] Patent Number: 5,531,662
[45] Date of Patent: Jul. 2, 1996

[54] DUAL MODE MICROWAVE/IONIZING PROBE

[75] Inventor: Kenneth L. Carr, Harvard, Mass.

[73] Assignee: Microwave Medical Systems, Inc., Littleton, Mass.

[21] Appl. No.: 170,064

[22] Filed: Dec. 20, 1993

Related U.S. Application Data

[63] Continuation-in-part of Ser. No. 126,106, Sep. 23, 1993, Pat. No. 5,364,336, which is a continuation of Ser. No. 995,326, Dec. 23, 1992, abandoned, which is a continuation of Ser. No. 628,579, Dec. 17, 1990, abandoned.

[51] Int. Cl.$^6$ ........................................ A61N 5/02
[52] U.S. Cl. ............................ 600/2; 607/101; 607/156
[58] Field of Search ........................ 600/1–3, 6–8; 128/804, 897–899; 607/100, 101, 154–156

[56] References Cited

U.S. PATENT DOCUMENTS 1,786,373  12/1930  Walker .
3,927,325  12/1975  Hungate et al. .
4,292,960  10/1981  Paglione .

FOREIGN PATENT DOCUMENTS 8502779  7/1985  WIPO .

*Primary Examiner*—Lee S. Cohen
*Assistant Examiner*—J. P. Lacyk
*Attorney, Agent, or Firm*—Cesari and McKenna

[57] ABSTRACT

A microwave radiator formed at least partially of a radioactive substance and adapted to simultaneously deliver microwave energy and nuclear radiation to living tissue. The radiator is incorporated into an interstitial or intracavitary probe. The radiator is a helical electrical conductor, formed of a radioactive substance such as iridium$^{192}$, and electrically connecting a central electrical conductor to a coaxial electrically-conducting jacket. Alternatively, a microwave antenna is formed as part of a probe with a cavity adapted to receive sources of ionizing radiation. Preferably, the cavity is part of a channel through a conduit carrying the probe, the channel being connected to a device for delivering ionizing radiation sources to the probe after positioning at the target tissue and after a heating regime. The device is able to remove the ionizing sources while leaving the microwave source in place for an additional heating regime. Other therapeutic regimes are facilitated by the combination.

14 Claims, 4 Drawing Sheets

DUAL MODE MICROWAVE/IONIZING PROBE

REFERENCE TO RELATED APPLICATIONS

This application is a continuation-in-part of application, Ser. No. 08/126,106, filed 23 Sep. 1993, now U.S. Pat. No. 5,364,336, which is a continuation of Ser. No. 07/995,326, filed 23 Dec. 1992, now abandoned, which was a continuation of Ser. No. 07/628,579, filed 17 Dec. 1990, now abandoned.

BACKGROUND OF THE INVENTION

This invention relates in general to methods and means for therapeutic medical treatment. More particularly, the invention involves an interstitial or intracavitary probe containing an antenna or radiator adapted to deliver microwave energy and ionizing radiation to living tissue within a human or animal body. The invention includes a novel method for simultaneously or sequentially delivering these forms of energy within ranges which are capable of destroying tumorous tissue while avoiding damage to viable tissue. This invention provides an efficient and effective means for implementing the synergistic necrotic effects of the simultaneous or sequential application of hyperthermia and ionizing radiation to tumors, and in particular deeply internal tumors, and particularly tumors of the brain, breast, esophagus, colon-rectum, cervix, vagina, bile duct, bronchus, and other sites now considered for interstitial or intracavitary radiation therapy.

In cancer therapy, failure to control local disease is a major cause of mortality and morbidity. Persistent local disease following conventional therapy occurs in about 30% of all the cases. Attempts at improving local control by radiosensitizers or combinations of chemo/radiotherapy have not had a significant impact. In cases where high doses of radiation can be delivered, the local control or cure rates have been excellent. In most cases, the dose limiting factor is the tolerance of the surrounding tissue. In order to overcome this difficulty, interstitial or intracavitary irradiation has been used for decades as an adjunct to external irradiation. At present, there is a resurgence in the use of intracavitary and interstitial irradiation due to several factors. These include the utilization of new radionuclides, the realization that the expected results of radiosensitizers or chemotherapy have not materialized, and the development of expertise by radiologists in the techniques of interventional radiology.

The results of previous studies using radiation and hyperthermia suggest that the response rates are double the response rate from radiation alone. It seems that the combination of hyperthermia and interstitial irradiation would be of benefit. Regions which would benefit the most from a hyperthermia-interstitial radiotherapy approach would include those cases where there is a high probability of local failure following external irradiation. Examples include brain tumors, sarcomas, melanomas, renal cell carcinoma, advanced head and neck and cervical cancer. Hyperthermia interstitial radiotherapy is also beneficial in treating cases where the surrounding tolerance of normal tissue limits the doses of external irradiation and hence curative external doses cannot be delivered. Examples would include carcinoma of the pancreas, esophagus, gall bladder and common bile duct.

The principle advantage of a technique combining interstitial radiation and hyperthermia would be the administration of irradiation and heat to a limited tumor volume while sparing the surrounding normal tissues.

At present, interstitial stereotactic radiotherapy in brain tumors is in progress. The development of an interstitial dual modality probe would provide an opportunity to enhance the radiation effectiveness in gliomas which are notorious for their radioresistance.

Cancer of the esophagus is rarely cured by irradiation although palliation is easily achieved. In Britain, several centers have adopted a new afterloading applicator to improve their results by intracavitary irradiation. Their aim is:

1. To convert inoperable patients to operable patients
2. Irradiate the entire esophagus with a localized high dose
3. Boost external beam therapy
4. Obtain cheap, quick palliation in incurable cases Combining these techniques with hyperthermia should result in significant clinical improvement.

Intracavitary techniques can also be used to improve the results in carcinoma of the common bile duct. Several recent reports have shown that combined external and interstitial irradiation is producing better results than surgery or irradiation alone. When combined with hyperthermia, intracavitary results should be even more impressive.

Limited lung cancer that is non-resectable due to adherence to surrounding structures are benefitted by interstitial radiotherapy. Again, combination with hyperthermia should yield better results.

Pancreatic cancers at present are treated mainly for palliation because of poor tolerance of surrounding tissue to external irradiation. Interstitial radiotherapy with hyperthermia should prove beneficial since most of those patients, many of whom die from local failure, undergo surgery and could have interstitial radiotherapy combined with local hyperthermia.

Often, potentially resectable tumors cannot be totally resected because the disease is adjacent to sensitive organs such as blood vessels or nerves. In these cases, external irradiation is often limited to the tolerance of surrounding tissue. The use of both hyperthermia and interstitial radiotherapy will allow curative doses of radiotherapy and a reduced dose to normal tissues due to the interstitial approach to radiation therapy.

Other areas where local control of disease is less than optimal includes recurrent head and breast cancer. In all of these cases, interstitial radiotherapy and hyperthermia should result in improved local control and better osmesis.

In short, the dual modality probe could initially be used in cases of recurrent tumors or accessible superficial lesions where implantation is indicated. It has wide implication for palliation, adjuvant and curative treatment.

The use of interstitial techniques in hyperthermia was suggested in 1975. Because of the complexity of the treatments and the collaboration required between disciplines of clinical hyperthermia and brachytherapy, very few centers have been dealing with these interstitial procedures.

The hyperthermia group at Tucson (University of Arizona) was one of the first to develop clinical interstitial forms of thermo-radiotherapy. They used resistive diathermy by means of radiofrequency electric currents (in a range 0.5–1 MHz) driven between pairs of arrays of implanted metallic needles. These needles were then loaded with $Ir^{192}$ wires, the complimentary radiation dose being approximately half the value of the usual "curative" brachytherapy dose.

Considering the encouraging preliminary results obtained in Tucson, several groups began to use interstitial resistive diathermy either in the same way or with modified techniques.

At the same time, other centers were developing means of producing interstitial thermotherapy using radiative heating by means of microwave antenna inserted into implanted plastic catheters using a frequency range from 300–1000 MHz. In general, this technique was followed by brachytherapy.

Other groups, particularly in the United States, are studying the use of implanted ferromagnetic seeds which can be inductively heated by high frequency, alternating magnetic fields. Newly designed, self-regulating thermoseeds using a Curie point switch have shown some promise.

In the data obtained in these centers, it appeared that interstitial techniques were able to achieve the required increase in tumor temperature in a large number of cases. In addition, the distribution of temperature was usually satisfactory with acceptable temperature profiles in the heated volume. The development of a technique as proposed in this document will ultimately make this thermo-radiation therapy approach more appealing to many physicians because of reduced complexity, ease of use and commercial availability of proven technology.

Hyperthermia has been studied extensively to determine its efficacy in the treatment of human neoplasm. In vitro work has demonstrated that hyperthermia can kill mammalian cells in a temperature and time dependent manner. The degree of cell kill has been shown to depend upon many factors. The microenvironment of the tumor is often conducive to hyperthermia cell killing because of such factors as low pH, anoxia, nutrient deficiency and altered cell cycle distribution. Hyperthermia as a sole modality is felt to have little potential value, but in combination with radiotherapy, preliminary studies are very positive.

The exact mechanism for thermal radio sensitization is not known. However, the mechanism is known to be synergistic and has a time-temperature dependence. The complimentary nature of these two modalities must not be understated. Typically, the conditions for radioresistance such as hypoxia, low pH, and cells in S phase are the conditions under which hyperthermia is most effective.

A significant amount of data has been complied to describe (if not explain) the synergistic nature of thermal radiotherapy. The reduction of the radiation survival curve would indicate an inhibition in the cells ability to accumulate and repair sublethal damage (SLD).

The rationale for the use of hyperthermia in conjunction with radiotherapy is well established. The role of hyperthermia in combination with interstitial low dose rate (LODR) radiotherapy may be even more important. It is well known that the combined application of heat and radiotherapy is more effective than exclusive use of either therapy. Simultaneous or overlapping treatment of heat and radiotherapy is inherent with the type of probe proposed. A second very important reason for designing a probe of the nature being proposed is the correlation between thermal sensitization and radiation damage as a function of radiation dose rate. Several studies have shown that the degree of thermal enhancement of radiation sensitivity is greater at low dose rates. For intracavitary and interstitial radiotherapy, the dose rate at the tumor periphery will be of the order of 40 rads/hour, which is typical of LDR radiotherapy.

Thus, while the therapeutic value of the combined application of ionizing radiation and hyperthermia are recognized, the systems for providing this synergistic benefit have been primarily of an experimental nature and characterized by complex, expensive, and cumbersome equipment inappropriate for use in day to day clinical environment.

These and other difficulties experienced with prior art devices have been obviated in a novel manner by the present invention.

It is, therefore, an outstanding object of this invention to provide a compact antenna or radiator capable of simultaneously or sequentially delivering microwave energy and ionizing radiation to tissue within a living organism.

It is another object of the invention to provide a probe bearing a microwave antenna which is adapted for insertion of an ionizing radiation source.

It is a further object of the invention to provide a device for warming target tissue with a probe carrying a microwave antenna and then subsequently introducing an ionizing radiation source via the same probe.

Another object of this invention is to provide a device which allows withdrawal of the ionizing radiation source while microwave heating continues.

Another object of this invention is the provision of a microwave and ionizing radiator which is simple in construction and use and capable of a long and useful life with a minimum of maintenance and expense.

With these and other objects in view, as will be apparent to those skilled in the art, the invention resides in the combination of parts set forth in the specification and covered by the claims appended hereto.

SUMMARY OF THE INVENTION

This invention is a therapeutic system for the simultaneous or sequential delivery of microwave energy and ionizing radiation to tissue within a living organism in order to provide synergistic hyperthermia and radiation treatment to the tissue. The system allows an optimization which maximizes therapeutic effect while minimizing undesirable side-effects. The system includes a conventional microwave generator and a conventional conduit which delivers microwave energy to a novel probe. In one aspect, the probe, which is adapted for interstitial or intracavitary invasion of the living organism, includes a novel antenna or radiator. The radiator is of conventional microwave radiator design except that it includes a source of ionizing radiation. More specifically, at least a portion the radiator is actually formed of a radioactive substance and preferably iridium$^{192}$. The radioactive substance may be either all or a part of the helical element of a conventional microwave radiator, may form the central conductor of a conventional microwave radiator or, in another aspect of the invention, may be fitted within a hollow core of the central conductor.

In one embodiment the probe is inserted into the living organism and placed adjacent the tissue to be treated. Then the radiator within the probe is caused to radiate microwave energy which causes hyperthermia within the target tissue. Simultaneously, the radioactive substance within the probe radiates ionizing radiation which treats the target tissue.

In a typical application, the radiator would be at the end of a coaxial cable having a central conductor and a coaxial conducting jacket. The radiator would be an iridium$^{192}$ wire formed in a helix coaxial with the central conductor, extending beyond the end of the conduit, and electrically connecting the central conductor with the jacket. When microwave current is generated by a microwave source and delivered through the conduit, it causes the helical antenna to radiate microwave energy which causes the heating of adjacent living tissue.

Another aspect of the invention involves integration of the ionizing radiation source into the antenna in a manner other than making a portion of the microwave source out of radioactive material.

This can involve making a cavity or cavities in the probe, for example, by providing a hollow central conductor, into which the ionizing source(s) can be inserted before the probe is applied to the target tissue.

Alternatively the entire length of the conduit carrying the probe may be provided with a channel (such as a hollow central conductor) or several independent channels into which the ionizing source(s) can be afterloaded after a preliminary heating regime and/or removed prior to a post-ionizing heating regime. If the tip of the probe is made of very thin-wall stainless steel, it offers little attenuation to the energy associated with the radioactive substance. Gold plating of the stainless steel tip, in turn, reduces the conductive losses at the microwave frequencies.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
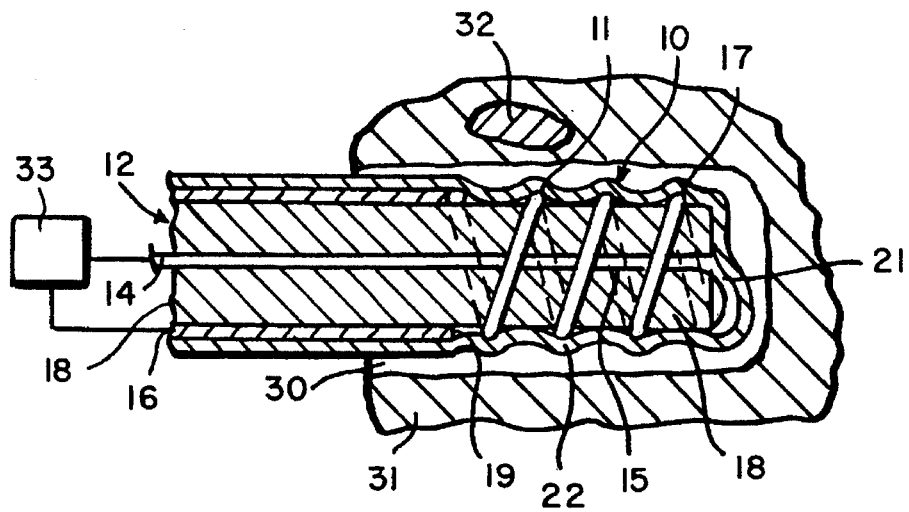
FIG. 1 is a cross-sectional view of a probe incorporating the principles of an embodiment of the present invention.

Referring first to FIG. 1, in which are shown the overall features of the present invention, the probe 10 of the system is intended to be inserted into a body cavity 30 or duct of a living organism 31 for treating target tissue 32 within the body with radio-frequency energy in the microwave frequency band, and with nuclear radiation. This insertion would normally be accomplished by feeding the probe through the lumen of a conventionally pre-placed catheter. The probe 10 is fixed to the end of a coaxial line or conduit 12. The coaxial line comprises the usual central conductor 14, outer conductor or jacket 16, and dielectric 18 between them. The conduit provides radio-frequency input (microwave), to the probe 10. In the preferred embodiment, the conduit ends at the end 19 of the conductive jacket 16. That portion 15 of the central conductor 14 which extends beyond the end 19 of the conductor 16 will be considered a part of the radiator 11. Portion 15 extends coaxially beyond the end of the jacket 16 and has an end 21. A coil or coils of a third helical conductor 17 surround the end portion 15 and dielectric 18 which envelopes the portion 15. The third conductor 17 is, by conductive connection, connected in series between the end 19 of the outer conductor 16 and the end 21 of the end portion 15. The radiator 11 is formed of the helix 17 and the portion 15. A smooth insulating dielectric sleeve 22 surrounds the helix 17 and the immediately-adjacent portion of the outer conductor 16.

It will be understood by those familiar with the art of microwave radiators that, while the helical antenna is preferred in this situation, monopoly or other antenna structures could be employed.

In order to provide the source of nuclear radiation, some portion of the probe 10 and preferably of the radiator 11 will be formed of a radioactive substance, preferably iridium$^{192}$.

In operation, the probe 10 would be inserted into a cavity 30 of a living organism 31 and positioned adjacent or within the target tissue 32. The microwave generator 33 would be activated. This would cause the conduit to convey microwave frequency current to the radiator and cause the radiator to radiate microwave energy into the target tissue 32 (and other adjacent tissue). Simultaneously, the portion of the radiator which is formed of radioactive material would be radiating ionizing radiation which would also irradiate the target tissue 32.

Figure 2:
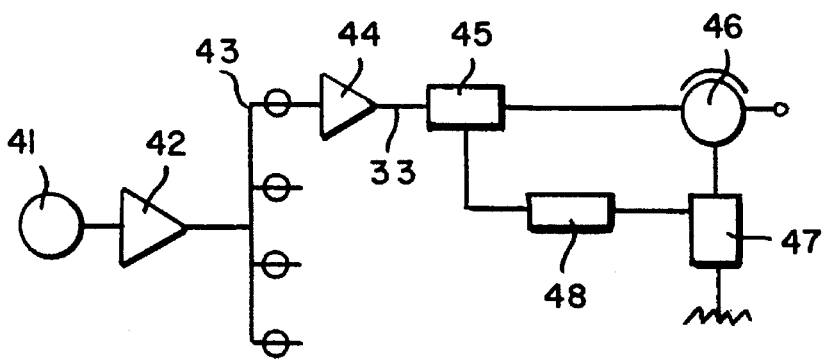
FIG. 2 is a schematic diagram of the microwave generator employed in the present invention.

A 915 MHz computer controlled microwave generator 33 (FIG. 2) will consist of a crystal controlled oscillator 41 driving a GaAs preamplifier 42. The signal will then be divided in phase by an N-way power divider such as a 4-way power divider 43 and each channel will be amplified by a 25 watt power amplifier (e.g. 44) to provide four channels of synchronous 25 watts output each. Each channel may be adjusted manually or by computer to any desired output power. Since the outputs are synchronous they may be combined to produce a total of 100 watts. The forward and reflected power will be monitored for each of the four channels with a power detector 45, circulator 46, and reverse power detector 47. These power measurements are displayed through a radiometer 48 as a percentage of the actual power. The number of antennas can be any number from one to several.

It should be understood that, while 915 MHz is the preferred frequency for this application, other microwave frequencies may be employed.

A number of aspects are important to the design of the radiator itself.

The physical aspects of the antenna affecting optimization are the heating pattern, the irradiation pattern and the fabrication techniques. In general, the heating pattern of helical antennas has been established. However, it is recognized that using Ir wire in place of copper (since Ir has a higher resistivity) may require slight modifications to the helical pattern. The nuclear irradiation pattern which is optimal results from a configuration in which only the helix 17 is formed of Iridium. Two alternate configurations are possible. The center conductor portion 15, only, could be made of Ir or both the center conductor portion 15 and the helix 17 could be made of Ir.

In the preferred embodiment, the helical antenna 17 would be fabricated using stable Ir and then the Ir portion of the antenna would be activated by neutron activation. This would mean that the entire antenna could be fabricated with no radiation hazards. The rationale for this approach is that Ir occurs in nature composed of two stable isotopes, $Ir^{191}$ (37%) and $Ir^{193}$ (63%). $Ir^{191}$ has a neutron cross section of 300 barns and $Ir^{193}$ has a cross section of 110 barns. Under neutron activation, $Ir^{193}$ goes to $Ir^{194}$ which decays with a half life of 19.2 hours and $Ir^{191}$ goes to $Ir^{192}$ whose decay scheme is attached with photon energies ranging from 300–610 KeV (average energy of 350 KeV) and a half life of 74.2 days. In fact, for radiotherapy work after neutron activation, the Ir wire is stored to allow $Ir^{194}$ to decay to low levels since its decay scheme is not desired in treatments. The two other materials present in the antenna would be copper (Cu) and teflon. The components of teflon all have neutron cross sections measured in millibarns and will therefore not produce any substantial unstable isotopes. The Cu portions of the antenna will be activated. Naturally occurring Cu consists of two isotopes, $Cu^{63}$ (69%) and $Cu^{65}$ (31%) with neutron cross sections of 4.5 barns and 2.3 barns, respectively. However, under neutron activation the isotopes produced, $Cu^{64}$ and $Cu^{66}$, have half lives of 12.7 hours and 5.1 minutes, respectively. It is therefore possible to activate the entire antenna and, during the waiting period normally used to allow the $Ir^{194}$ to decay, all other unstable isotopes of appreciable quantity will also have decayed to suitable levels.

Although the above-described process is preferred, several alternate techniques are possible including:
1. making the center conductor portion 15 of Ir and then activating with neutron activation
2. making the center conductor portion 15 hollow and inserting $Ir^{192}$, just prior to treatment
3. fabricating the antenna with $Ir^{192}$ at a facility licensed to handle radioactive materials.

Three antenna designs are contemplated for use with the 915 MHz microwave generator. All three will be helical in three distinctly different sizes. The physical size of the helix in relation to the medium wavelength determines the antenna field patterns. The designed helical antennas will operate in one of two modes, the "normal mode" and the "axial mode". In the normal mode of operation, the actual coiling length of the helix is small compared to the medium wavelength and the maximum radiation is always in the direction normal to the helix axis. The normal mode antennas will be designed for circular polarization to ensure an even thermal pattern along side the antenna. In this case, the ratio of the circumference of the coils to the medium wavelength is equal to the square root of the product of two times the spacing between coils divided by the medium wavelength.

In the axial mode of operation, the circumference of the helix is to be approximately a wavelength for circular polarization and the optimum spacing is approximately one-quarter wavelength.

The physical size of the helix in relation to the medium wavelength determines the antenna field patterns. With two modes of operation and three possible antenna designs, the tumor site can be treated more optimally. The three antennas are fabricated with teflon-insulated copper tubing. The copper center conductor will be soldered or welded to the iridium helix at the tip. Thus, the helix itself will be formed using iridium wire. The antennas will be designed as follows:

1. The basic antenna which operates in the normal mode application with the copper helix replaced with iridium, and used on radial target tissue near the cavity,
2. An antenna with a slightly larger diameter to create a greater thermal radiation pattern in the normal mode, for use on radial target tissue further from the cavity,
3. A longer, slimmer antenna that operates in the axial mode.

Figure 3:
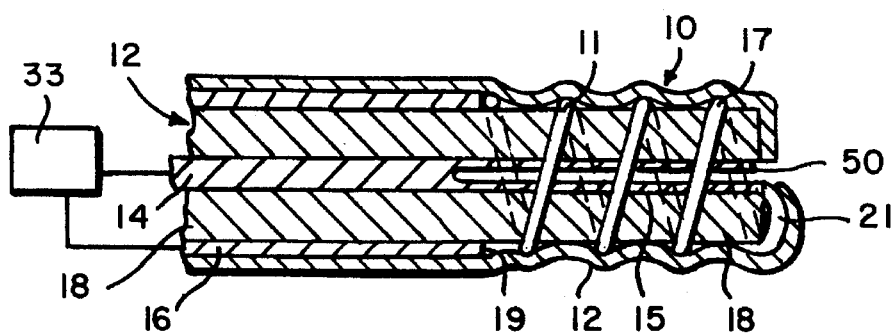
FIG. 3 is a cross-section of a probe having a cavity for insertion of an ionizing source or sources.
Figure 4:
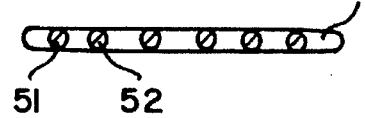
FIG. 4 shows a plurality of ionizing sources adapted for insertion in the prove of FIG. 3.

One alternative embodiment of the invention is shown in FIGS. 3 and 4. In this embodiment, the tip of the probe is provided with a cavity 50 adapted to receive a plurality of ionizing radiation sources or "seeds" such as 51 and 52. The seeds are preferably incorporated in a capsule 55. The seeds are arranged to provide a pre-established dose distribution determined by the extent of diseased tissue and the desired treatment regime.

In the embodiment of FIG. 3, the cavity 50 is formed as a hollow part of the portion 15 of the central conductor, but may alternatively be a separate cavity in the probe.

Figure 5:
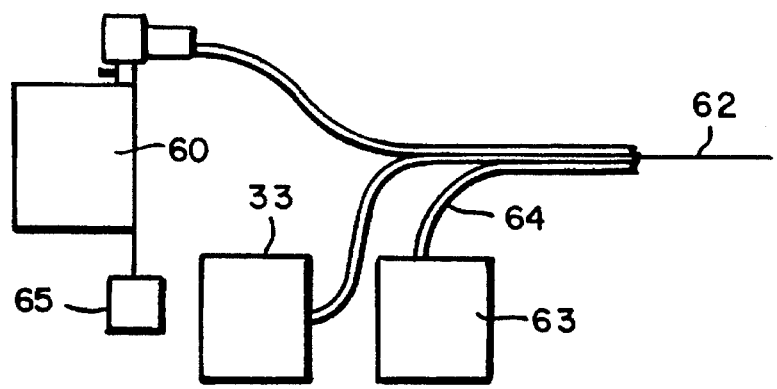
FIG. 5 is a schematic view of a system incorporating an automatic ionizing source loader, a microwave heater and fiber optics.

Alternatively and preferably, the ionizing sources may be introduced into the microwave heating probe after insertion and positioning near the target tissue. In the setup shown schematically in FIG. 5 an afterloading device 60 for ionizing sources is configured to load the ionizing sources through the same conduit and probe assembly 62 that carries power from the microwave power source 33 to the target tissue 32. The afterloading device 60 may be, for example, the automatic brachytherapy device sold under the trademark GAMMAMED by ISOTOPEN-TECHNIK DR. SAUERWEIN GMBH of Haan/Rheinland, Germany. In addition, the usefulness of the system may be enhanced by the provision of an adjunct endoscopic assembly 63 including fiberoptics 64 to provide light and visualization of the target area.

Systems, such as system 65, are available for automatically optimizing ionizing treatment planning and control, including spatial and temporal control of insertion and removal of ionizing sources.

Figure 6:
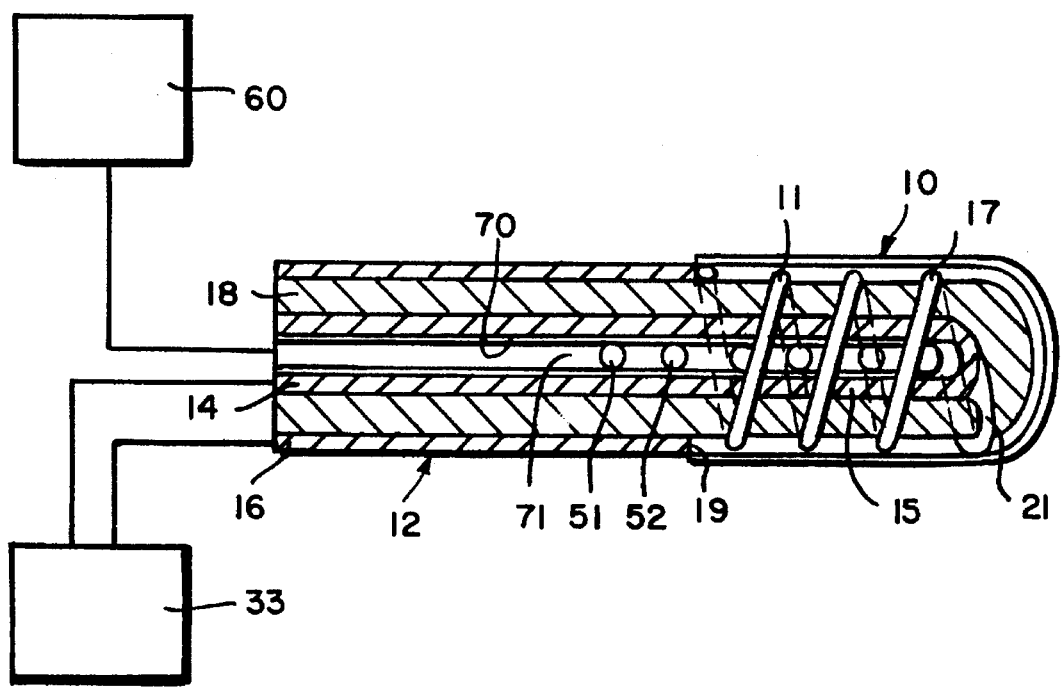
FIG. 6 shows a conduit and probe adapted for loading ionizing sources after insertion of the probe adjacent the target tissue.

More particularly, FIG. 6 shows a portion of a conduit 12 and a probe 10 combining the elements of a microwave heating device with elements of a remote ionizing source loading device. The microwave power source 33 is connected to the central conductor 14 and the conductive jacket 16 to provide microwave power to the antenna or radiator 11. The radiator is this embodiment is again a helix although other radiator configurations are possible. In particular, see U.S. Pat. No. 4,557,272 which is hereby incorporated by reference. In this embodiment, however, a channel 70 is provided in the conduit 12 and probe 10 which channel is adapted for insertion of an applicator 71 from the ionizing source loading device 60. Although in this embodiment the channel constitutes the hollow core of the central conductor, the channel may also be independent of, and parallel to, the central conductor. Moreover, several channels may be provided to accommodate the gradual loading and unloading of the ionizing sources. This allows a step-wise construction of the curve of the ionizing radiation regime. The ionizing source seeds such as 51 and 52 are loaded at the predetermined locations and times for the desired treatment regime using pneumatic or mechanical methods.

The portion of the probe adapted to hold the ionizing or radioactive sources is preferably made of very thin stainless steel so that it offers little attenuation to the energy associated with the radioactive substance. Gold plating of the stainless steel, in turn, reduces the conductive losses at microwave frequencies.

Using the configuration of FIG. 6, it is possible to optimize the heating/ionizing regime using a single probe and without removing the probe itself during treatment. Often the optimum heating time is significantly longer than the optimum ionizing radiation time. It is also useful to begin the heating regime prior to ionization therapy and to continue the heating regime after ionizing radiation therapy.

Figure 7:
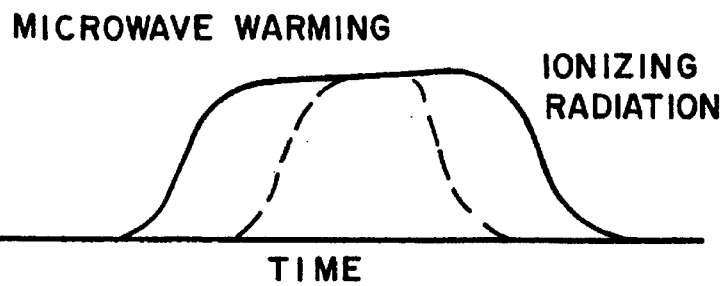
FIGS. 7, 8, 9, and 10 are qualitative graphs of regimes of heating and ionizing radiation for which the probe of FIG. 6 is especially designed.

This therapy regime is shown qualitatively in the graph of FIG. 7.

Such a regime can be easily carried out using the configuration of FIG. 6. Heating of the target tissue can be carried out before deployment of the ionizing radiation sources. After the desired heating regime, the insertion of ionizing radiation sources can be carried out as with standard afterloading technique. Heating can be accomplished before, during, and after ionizing radiation since the microwave antenna need not be removed when the ionizing sources are removed.

Figure 8:
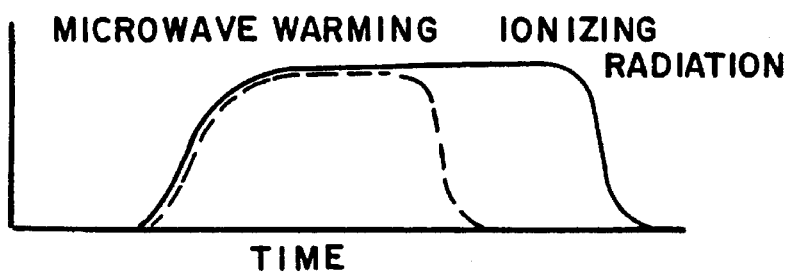
Figure 9:
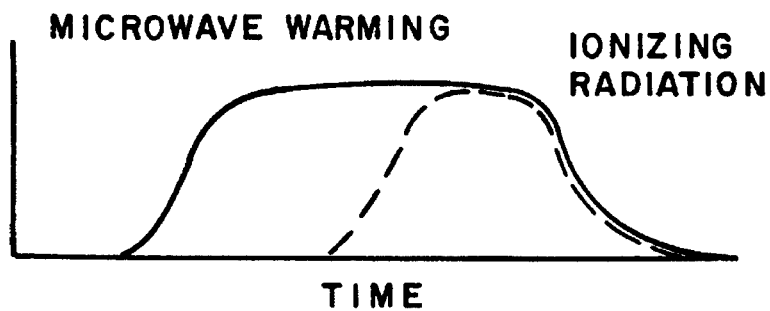

Likewise, as shown in FIGS. 8 and 9, other regimes are facilitated by the combination of microwave heating and afterloaded ionizing sources. As shown in FIG. 8, the warming and ionizing may be initiated substantially simultaneously and then the ionizing sources removed while warming continues. Or, as in FIG. 9, a warming regime may precede the combined therapy, with both modalities being discontinued substantially simultaneously.

Figure 10:
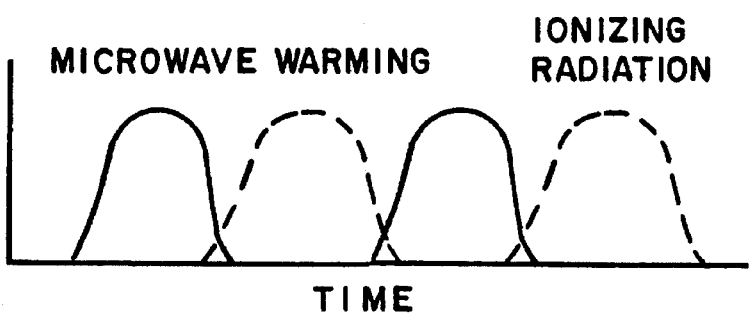

More complex regimes are also facilitated by the present invention. For example, as shown in FIG. 10, warming may be applied and stopped, followed by a predetermined period of ionizing radiation; this cycle may then be repeated as desired.

Figure 11:
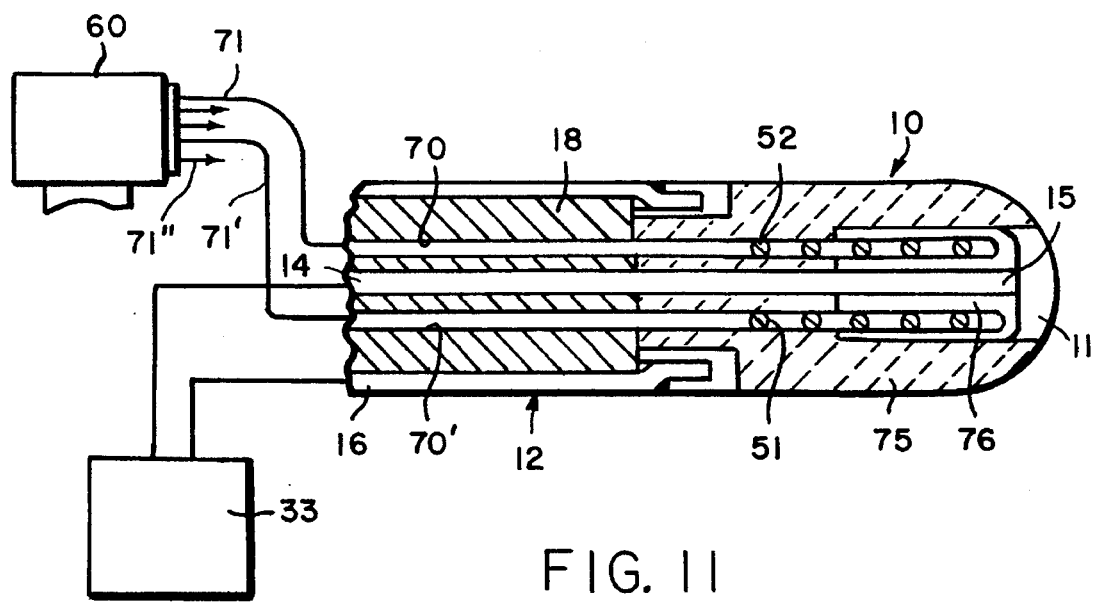
FIG. 11 shows an alternative embodiment, having several channels independent of the central conductor.

As previously indicated, the conduit and probe may be provided with multiple channels for afterloading ionizing sources, and these channels may be independent of the central conductor. In the embodiment shown in FIG. 11, the conduit 12 and probe 10 may be provided with a radiator or antenna 11 contained within a ceramic end 75 and comprising a portion 15 of the central conductor 14 and a launch assembly 76. In this case, the antenna is non-helical. Several channels such as 70 and 70' are provided, passing through the dielectric 18 of the conduit and into the probe to terminate adjacent the antenna 11. The channels are adapted to receive the applicators such as 71, 71', and 71" from the afterloading device 60. As above, a plurality of ionizing sources such as seeds 51 and 52 are introduced through the channels 70 and 70' for the desired time periods and at the desired locations adjacent the antenna. The antenna is provided with microwave power from a power source 33 connected to the central conductor 14 and the outer conductor 16.

Figure 12:
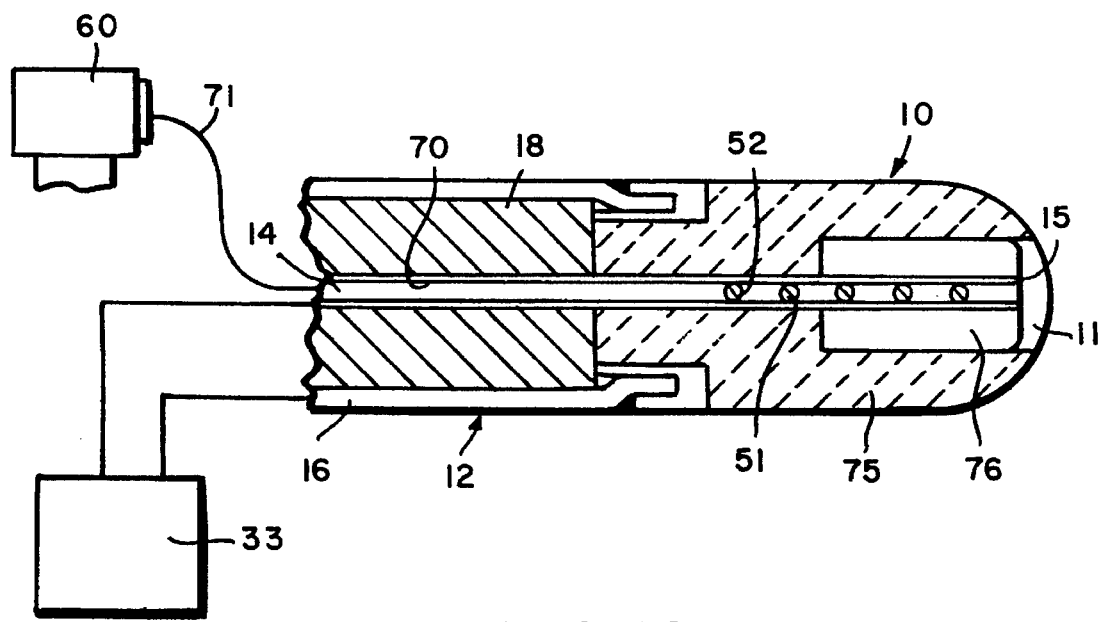
FIG. 12 shows another alternative embodiment, a non-helical antenna with a hollow central conductor.

Also, as previously indicated, the conduit and probe may be provided with a channel for afterloading ionizing sources, and this channel may be the hollow central conductor of a non-helical antenna. In the embodiment shown in FIG. 12, the conduit 12 and probe 10 may be provided with a radiator or antenna 11 contained within the ceramic end 75 and comprising a portion 15 of the central conductor 14 and a launch assembly 76. In this case, the antenna is non-helical. A channel 70 is provided, passing through the dielectric 18 of the conduit and into the probe to terminate within the antenna 11. The channel is adapted to receive the applicator 71, from the afterloading device 60. As above, a plurality of ionizing sources such as seeds 51 and 52 are introduced through the channel 70 for the desired time periods and at the desired locations adjacent the antenna. The antenna is provided with microwave power from a power source 33 connected to the central conductor 14 and the outer conductor 16. The tip of this embodiment can be a hollow, thin-walled stainless steel structure or it can be a plated ceramic which is hollowed on the inside to allow for acceptance of the radioactive material.

It is apparent that minor changes may be made in the form and construction of the invention without departing from the material spirit thereof. It is not, however, desired to confine the invention to the exact form herein shown and described, but is desired to include all such as properly come within the scope claimed.

The invention having been thus described, what is claimed as new and desired to secure by Letters Patent is:

1. A therapeutic system for delivery of microwave radiation and ionizing radiation to living tissue comprising:

a microwave current generator, a coaxial conduit having a central electrical conductor and a coaxial electrically-conducting jacket and having a first end connected to the generator and a second end, a microwave antenna attached to said conduit second end, said antenna being adapted to be placed adjacent living tissue, a radiation source-receiving cavity in said conduit, said cavity extending to a location in said conduit adjacent to said antenna, and an ionizing radiation source sized to be received in said cavity for placement at said location.

2. The therapeutic system as recited in claim 1, wherein said antenna includes a central conducting portion of said central electrical conductor and said cavity is formed in said central conducting portion.

3. The system as recited in claim 1, and further including a tip of thin-walled stainless steel at said conduit second end.

4. The system as recited in claim 3, wherein said tip is gold-plated.

5. A system as recited in claim 1, wherein said cavity is separate from said central electric conductor.

6. The system as recited in claim 5, wherein said conduit has more than one cavity.

7. The system recited as in claim 1, and further including means for delivering said ionizing radiation source to said cavity.

8. The system as recited in claim 1, wherein said cavity is a channel which extends from said location to said conduit first end.

9. The system as recited in claim 1, wherein said cavity is a channel which extends from said location to said conduit second end.

10. A dual mode therapeutic system for delivery of radiation to living tissue, said system comprising:

antenna means defining an antenna having a radiating end and an opposite end, said antenna means including a coaxial conduit having a central electrical conductor and an outer electrical conducting jacket, said conductor having an end portion extending beyond said jacket and an antenna conductor electrically connecting said central electrical conductor and said jacket, a radiation source-receiving cavity in said antenna means, said cavity being in said conductor end portion and extending to a location adjacent to said antenna radiating end, an ionizing radiation source sized to be received in said cavity for placement at said location, and means for connecting said antena means to a source of energy so that said system can deliver to said tissue thermo-radiation from said antenna radiating end and/or ionizing radiation from said source.

11. The system as recited in claim 10, and further including means for delivering said ionizing radiation source to said cavity.

12. The system as recited in claim 10, wherein said cavity is a channel which extends from said location to said antenna radiating end.

13. The probe as recited in claim 10, wherein said cavity extends from said location to said antenna opposite end.

14. The system defined in claim 10 wherein said antenna is a helical conductor electrically connecting said central conductor to said outer jacket.

* * * * *